United States Patent [19]
Goldmann et al.

[11] Patent Number: 4,904,665
[45] Date of Patent: Feb. 27, 1990

[54] BENZYLAMINOARYL-DIHYDROPYRIDINELACTONES AND THEIR USE IN MEDICAMENTS

[75] Inventors: Siegfried Goldmann; Rainer Gross; Martin Bechem, all of Wuppertal; Michael Kayser, Hagen; Matthias Schramm, Cologne; Siegbert Hebisch, Oberhausen, all of Fed. Rep. of Germany

[73] Assignee: Bayer Aktiengesellschaft, Leverkusen, Fed. Rep. of Germany

[21] Appl. No.: 158,184

[22] Filed: Feb. 18, 1988

[30] Foreign Application Priority Data

Feb. 26, 1987 [DE] Fed. Rep. of Germany ....... 3706204

[51] Int. Cl.4 ................... A61K 31/44; C07D 491/048
[52] U.S. Cl. .................................... 514/256; 514/302; 544/333; 546/116
[58] Field of Search ............... 546/116; 514/302, 256; 544/333

[56] References Cited

U.S. PATENT DOCUMENTS 4,532,248  7/1985  Franckowiak et al. ............. 514/302
4,804,667  2/1989  Goldmann et al. ................. 546/116

FOREIGN PATENT DOCUMENTS 0071819  2/1983  European Pat. Off. .
0231511  8/1987  European Pat. Off. .
1552911  9/1979  United Kingdom .

OTHER PUBLICATIONS

Wagner and Zook, Synthetic Org. Chem., Wiley & Sons, N.Y.C., pp. 666–667, (1953).
Pharmazie Heute, Band 3, No. 104, 1983, Seiten 139–146; R. Manhold et al.: "Pharmakologische Differenzierung von Calcium–Antagonisten".
Chemical Abstracts, Band 85, No. 7, Aug. 16, 1976, Seite 511, Zusammengassungsnr., 46396s, Columbus, Ohio, U.S.; & JP-A-75 131 972.

Primary Examiner—Mary C. Lee
Assistant Examiner—Bernard I. Dentz

Attorney, Agent, or Firm—Sprung Horn Kramer & Woods

[57] ABSTRACT

A benzylaminoaryl-dihydropyridinelactone compound of the formula (I)

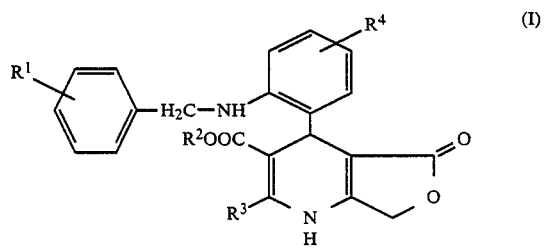

in which
$R^1$ represents hydrogen, halogen, cyano, nitro, $C_6$–$C_{12}$-aryl, $C_1$–$C_8$-alkyl, $C_1$–$C_8$-alkoxy, $C_1$–$C_6$-alkylthio, trifluoromethyl, trifluoromethoxy, trifluoromethylthio, difluoromethoxy, di-$C_1$–$C_5$-alkylamino, $C_1$–$C_6$-alkoxycarboxyl or $C_1$–$C_6$-alkylsulphonyl,
$R^2$ represents hydrogen, or represents a straight-chain, branched or cyclic, saturated or unsaturated hydrocarbon radical having up to 10 carbon atoms which is optionally substituted by $C_1$–$C_6$-alkoxy, $C_1$–$C_6$-alkylthio, $C_1$–$C_6$-alkylsulphonyl, halogen, cyano, hydroxyl, pyridyl, thienyl, pyrimidyl, piperidinyl, phenyl or an amino group, where the amino group carries two identical or different substituents from the series comprising $C_1$–$C_5$-alkyl, phenyl or benzyl,
$R^3$ represents $C_1$–$C_5$-alkyl, or represents cyano, hydroxymethyl or formyl, and
$R^4$ represents hydrogen, halogen, $C_1$–$C_5$-alkyl or trifluoromethyl, and its isomers, isomeric mixtures, racemates or optical antipodes, and physiologically acceptable salts thereof. The compound being useful to improve the contractility of the heart and the tonus of the smooth muscles.

7 Claims, No Drawings

BENZYLAMINOARYL-DIHYDROPYRIDINELACTONES AND THEIR USE IN MEDICAMENTS

BACKGROUND OF THE INVENTION

The invention relates to benzylaminoaryl-dihydropyridinelactones, a process for their preparation, and their use in medicaments, in particular in circulation-influencing medicaments.

SUMMARY OF THE INVENTION

The present invention relates to benzylaminoaryl-dihydropyridinelactones of the general formula (I)

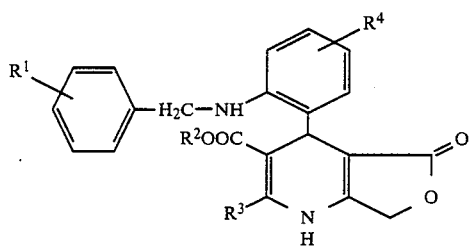

in which
- $R^1$ represents hydrogen, halogen, cyano, nitro, $C_6-C_{12}$-aryl, $C_1-C_8$-alkyl, $C_1-C_8$-alkoxy, $C_1-C_6$-alkylthio, trifluoromethyl, trifluoromethoxy, trifluoromethylthio, difluoromethoxy, di-$C_1-C_5$-alkylamino, $C_1-C_6$-alkoxycarbonyl or $C_1-C_6$-alkylsulphonyl,
- $R^2$ represents hydrogen, or represents a straight-chain, branched or cyclic, saturated or unsaturated hydrocarbon radical having up to 10 carbon atoms which is optionally substituted by $C_1-C_6$-alkoxy, $C_1-C_6$-alkylthio, $C_1-C_6$-alkylsulphonyl, halogen, cyano, hydroxyl, pyridyl, thienyl, pyrimidyl, piperidinyl, phenyl or an amino group, where the amino group carries two identical or different substituents from the series comprising $C_1-C_5$-alkyl, phenyl or benzyl,
- $R^3$ represents $C_1-C_5$-alkyl, or represents cyano, hydroxymethyl or formyl, and
- $R^4$ represents hydrogen, halogen, $C_1-C_5$-alkyl or trifluoromethyl, in the form of their isomers, isomeric mixtures, racemates or optical antipodes, and their physiologically acceptable salts.

DETAILED DESCRIPTION OF THE INVENTION

The compounds according to the invention may exist in the form of their salts. In general, these are salts of substances according to the invention with inorganic or organic acids. These are preferably physiologically acceptable salts of substances according to the invention with inorganic or organic acids. Examples which may be mentioned are: hydrohalides, such as, for example, hydrochlorides or hydrobromides, or hydrogen sulphates, sulphates, hydrogen phosphates, formates, acetates, propionates, maleates, citrates, fumarates, tartrates, lactates or benzoates.

The compounds according to the invention exist in stereoisomeric forms which behave either as image and mirror image (enantiomers) or do not behave as image and mirror image (diastereomers). The invention relates both to the antipodes and to the racemic forms and to the diastereomeric mixtures. The racemic forms can be resolved, as can the diastereomers, into the stereoisomerically unitary components in a known fashion (cf. E. L. Eliel, Stereochemistry of Carbon Compounds, McGraw Hill, 1962).

Compounds of the general formula (I) which may preferably be mentioned are those in which
- $R^1$ represents hydrogen, fluorine, chlorine, bromine, iodine, cyano, nitro, phenyl, $C_1-C_6$-alkyl, $C_1-C_6$-alkoxy, $C_1-C_4$-alkylthio, trifluoromethyl, trifluoromethoxy, difluoromethoxy, di-$C_1-C_3$-alkylamino, $C_1-C_4$-alkoxycarbonyl or $C_1-C_4$-alkylsulphonyl,
- $R^2$ represents hydrogen, or represents a straight-chain or branched hydrocarbon radical which has up to 8 carbon atoms and which may be substituted by $C_1-C_4$-alkoxy, $C_1-C_4$-alkylthio, $C_1-C_4$-alkylsulphonyl, fluorine, chlorine, bromine, iodine, cyano, hydroxyl, pyridyl, pyrimidyl, phenyl or by an amino group, where the amino group carries two identical or different substituents from the series comprising $C_1-C_3$-alkyl or benzyl,
- $R^3$ represents $C_1-C_3$-alkyl or cyano, and
- $R^4$ represents hydrogen, fluorine, chlorine, bromine, $C_1-C_3$-alkyl or trifluoromethyl, in the form of their isomers, isomeric mixtures, racemates or optical antipodes,
and their physiologically acceptable salts.

Compounds of the general formula (I) which may particularly preferably be mentioned are those in which
- $R^1$ represents hydrogen, fluorine, chlorine, bromine, nitro, phenyl, $C_1-C_4$-alkyl, $C_1-C_4$-alkoxy, trifluoromethyl or dimethylamino,
- $R^2$ represents straight-chain or branched alkyl which has up to 6 carbon atoms and which may be substituted by methoxy, fluorine, chlorine, cyano, hydroxyl, pyridyl, phenyl or N-benzyl-N-methylamino,
- $R^3$ represents methyl, and
- $R^4$ represents hydrogen, fluorine or chlorine, in the form of their isomers, isomeric mixtures, racemates or optical antipodes, and their physiologically acceptable salts.

The compounds of the general formula (I) according to the invention are obtained when amino compounds of the general formula (II)

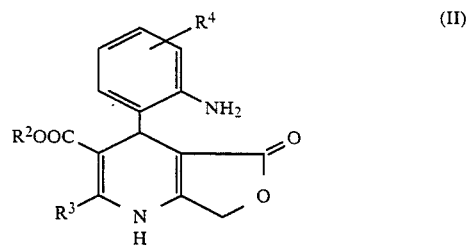

or their salts in which $R^2$, $R^3$ and $R^4$ have the above-mentioned meaning, are reacted with benzyl halides of the general formula (III)

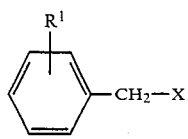

in which

R¹ has the abovementioned meaning, and

X represents halogen, preferably chlorine or bromine, if appropriate in the presence of bases and if appropriate in the presence of an inert solvent.

If methyl 4-(2-aminophenyl)-2-methyl-5-oxo-1,4,5,7-tetrahydrofuro[3,4-b]pyridine-3-carboxylate and benzyl chloride are used as starting materials, the reaction may be illustrated by the following equation:

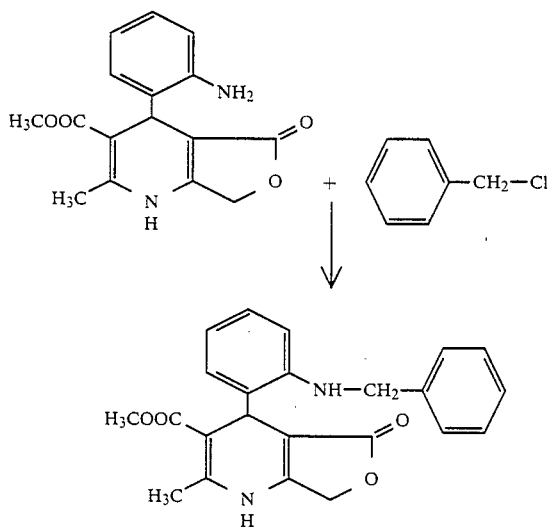

Suitable solvents are conventional organic solvents which are inert under the reaction conditions. These preferably include ethers, such as diethyl ether, butyl methyl ether, dioxane, tetrahydrofuran or glycol dimethyl ether, or halogenated hydrocarbons, such as methylene chloride, chloroform, carbon tetrachloride or 1,2-dichloroethane, or hydrocarbons, such as benzene, toluene, xylene, hexane or mineral oil fractions, or amides, such as dimethylformamide, dimethylacetamide or hexamethylphosphoric triamide, or ethyl acetate, acetone, acetonitrile, dimethyl sulphoxide or pyridine. It is likewise possible to employ mixtures of the solvents mentioned.

Suitable bases are conventional inorganic or organic bases. These preferably include alkali metal or alkaline-earth metal hydroxides, such as sodium hydroxide, potassium hydroxide or barium hydroxide, or alkali metal carbonates, such as sodium carbonate, sodium hydrogen carbonate or potassium carbonate, or alkali metal alcoholates, such as, for example, sodium methanolate, sodium ethanolate, potassium methanolate, potassium ethanolate or potassium tert.butanolate, or organic amines, such as trialkylamines, for example, triethylamine or ethyldiisopropylamine, or bases, such as pyridine, dimethylaminopyridine, quinoline, isoquinoline, methylpiperidine or methylmorpholine. Triethylamine or potassium carbonate are particularly preferably employed.

The reaction may be carried out in a temperature range from 0° C. to +100° C., preferably from +10° C. to +50° C.

The reaction may be carried out at atmospheric pressure, but also at increased or reduced pressure. In general, the reaction is carried out at atmospheric pressure.

In the reaction, the benzyl halide is generally employed in an amount from 1 to 3, preferably from 1 to 1.5, moles, relative to 1 mole of the amino compound. The base is generally employed in an amount from 1 to 5 moles, preferably from 1 to 2.5 moles, relative to 1 mole of the benzyl halide. Molar amounts of all reactants are particularly preferably used.

The amino compounds of the general formula (II) employed as starting compound, and their salts, are new and can be prepared by reducing nitro compounds of the general formula (IV)

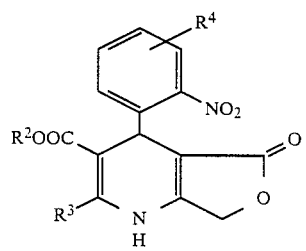

in which R², R³ and R⁴ have the abovementioned meaning, in a fashion which is known per se, if appropriate in the presence of a catalyst, if appropriate in the presence of an acid and if appropriate in the presence of an inert solvent.

If 2-methyl-4-(2-nitrophenyl)-5-oxo-1,4,5,7-tetrahydrofuro[3,4-b]pyridine-3-carboxylic acid methyl ester is used as starting material, the reduction may be illustrated by the following equation:

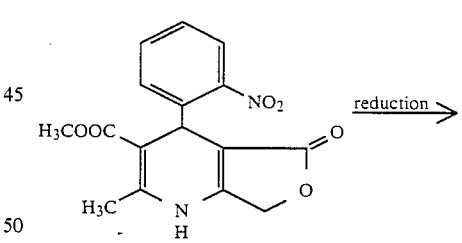

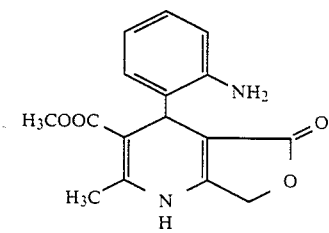

The reduction is carried out in a fashion which is known per se, preferably by hydrogenating using metal catalysts, such as, for example, platinum, palladium, palladium on animal charcoal or Raney nickel, in the presence of acids.

Acids which can be employed are strong mineral acids, but also organic acids. Hydrohalic acids, such as hydrochloric acid or hydrobromic acid, sulphuric acid, phosphoric acid or perchloric acid, or organic acids, such as acetic acid, trifluoro acetic acid, trichloro acetic acid, or methanesulphonic acid, ethanesulphonic acid, benzenesulphonic acid or, preferably, p-toluenesulphonic acid, are preferred.

The catalyst in this reduction is generally employed in an amount from 0.1 to 50 mol-%, preferably from 1 to 10 mol-%, relative to the nitro compound.

The hydrogenation is generally carried out in a temperature range from −20° C. to +100° C., preferably in the range from 0° C. to +50° C.

In general, the hydrogenation is carried out using an excess pressure of 5 to 100 bar, preferably from 10 to 80 bar, of hydrogen. It is likewise possible to carry out the hydrogenation at atmospheric pressure.

Suitable solvents for the hydrogenation are water and/or inert organic solvents. These preferably include alcohols, such as methanol, ethanol, propanol or isopropanol, or ethers, such as diethyl ether, dioxane, tetrahydrofuran, glycol monomethyl ether or glycol dimethyl ether, halogenated hydrocarbons, such as methylene chloride, chloroform or carbon tetrachloride, or glacial acetic acid, dimethylformamide, ethyl acetate or acetone. It is likewise possible to employ mixtures of the solvents mentioned.

The reduction is particularly preferably carried out using Raney nickel in alcohols using an excess pressure of hydrogen.

However, the reduction can likewise be carried out using metals, such as zinc, tin or iron, in the presence of acids, such as ethyl acetate or hydrochloric acid, as described by R. Schröter in Houben-Weyl's "Methoden der organischen Chemie" [Methods of organic chemistry] VI/1, 363 ff.

The nitro compounds of the general formula (IV) used as starting materials are known or can be prepared by known methods [DE-OS (German Published Specification) 3,206,671].

The compounds according to the invention exhibit a valuable pharmacological range of action which could not be foreseen. They influence the contractility of the heart and the tonus of the smooth muscles. They can therefore be employed in medicaments for influencing pathologically altered blood pressure, as coronary therapeutic agents and for treatment of heart insufficiency. In addition, they can be used for treating heart-rhythm disturbances, for lowering blood sugar levels, for shrinking mucous membranes and for influencing the salt and liquid balance.

The heart action was found on isolated ventricles of guinea pig hearts.

To this purpose, the left ventricle of guinea pig hearts are isolated, and suspended in an organ bath kept at a temperature of 32° C. A Krebs-Henselei solution having the following composition (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of NaEDTA and 1.8 mmol/l of $CaCl_2$) with addition of 10 mmol/l of glucose as energy-supplying substrate is used as the incubation medium. The solution is gassed with carbogen (95% of $CO_2$ and 5% of $O_2$) in order to maintain a pH of 7.4. The left ventricles are clamped in the organ bath, a certain basic tonus being set, and the tension is recorded by means of a force transducer. Under periodic electrical stimulation, the contractions following here are recorded continuously on a high-speed recorder. In the presence of the respective compounds according to the invention, a percentage change compared to the initial value, set at 100%, is produced in this procedure:

| Example | Concentration (g/l) | % change in contraction force |
|---|---|---|
| 4 | $10^{-3}$ | +57 |
| 5 | $10^{-3}$ | +33 |
| 6 | $10^{-3}$ | +109 |
| 7 | $10^{-3}$ | +120 |
| 8 | $10^{-3}$ | +54 |
| 9 | $10^{-3}$ | +56 |
| 10 | $10^{-3}$ | +80 |
| 12 | $10^{-3}$ | +70 |

The new active compounds can be converted in a conventional fashion into conventional formulations, such as tablets, coated tablets, pills, granules, aerosols, syrups, emulsions, suspensions and solutions, using inert, nontoxic, pharmaceutically suitable excipients or solvents, the therapeutically active compound is in each case present in these formulations in a concentration from about 0.5 to 90% by weight of the total mixture, i.e. in amounts which are sufficient to achieve the dosage lattitude specified.

The formulations are prepared, for example, by extending the active compounds with solvents and/or excipients, if appropriate using emulsifiers and/or dispersants, where, in the case of the use of water as diluent, for example, organic solvents may be used, if appropriate, as auxiliary solvents.

Auxiliaries which may be mentioned as examples are as follows:

water, nontoxic organic solvents, such as paraffins (for example, mineral oil fractions), vegetable oils (for example groundnut/sesame oil), alcohols (for example, ethyl alcohol and glycerol), excipients, such as, for example, ground natural minerals (for example, kaolins, clays, talc and chalk), ground synthetic minerals (for example, highly dispersed silica and silicates) and sugars (for example, cane sugar, lactose and glucose), emulsifiers (for example, polyoxyethylene fatty acid esters, polyoxyethylene fatty alcohol ethers, alkylsulphonates and arylsulphonates), dispersants (for example, lignin, sulphite waste liquors, methylcellulose, starch and polyvinyl pyrrolidone) and lubricants (for example, magnesium stearate, talc, stearic acid and sodium lauryl sulphate).

Administration takes place in a conventional fashion, preferably orally or parenterally, in particular perlingually or intravenously. In the case of oral administration, tablets can, of course, also contain, in addition to the excipients mentioned, additives such as sodium citrate, calcium carbonate and dicalcium phosphate, together with various additional substances, such as starch, preferably potato starch, gelatin and the like. Furthermore, lubricants, such as magnesium stearate, sodium lauryl sulphate and talc, can be co-used when making tablets. In the case of aqueous suspensions, the active compounds can be mixed with various flavor-improving agents or colorants, in addition to the above-mentioned auxiliaries.

In the case of parenteral administration, solutions of the active compounds can be employed using suitable liquid excipient materials.

In general, it has proved advantageous to administer amounts from about 0.001 to 1 mg/kg, preferably about 0.01 to 0.5 mg/kg of body weight in order to achieve effective results in the case of intraveneous administration, and dosage in the case of oral administration is about 0.01 to 20 mg/kg, preferably 0.1 to 10 mg/kg of body weight.

Nevertheless, it may at times be necessary to deviate from the amounts mentioned, and in particular to do so as a function of the body weight and of the nature of the administration method, the individual behaviour towards the medicament, the nature of the formulation of the medicament and the time or interval over which the administration takes place. Thus, it may be sufficient in some cases to manage with less than the abovementioned minimum amount, whilst in other cases the upper limits mentioned must be exceeded. In the case of administration of relatively large amounts, it may be advisable to divide these into several individual administrations over the course of the day.

PREPARATION EXAMPLES

Example 1

Ethyl 4-(2-aminophenyl)-2-methyl-5-oxo-1,4,5,7-tetrahydrofuro[3,4-b]pyridine-3-carboxylate hydrochloride

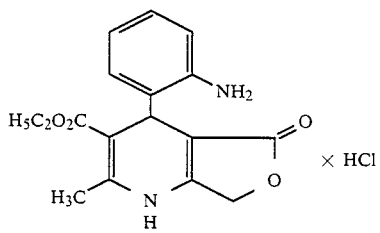

58 mmol of ethyl 4-(2-nitrophenyl-2-methyl-5-oxo-1,4,5,7-tetrahydrofuro[3,4-b]pyridine-3-carboxylate are dissolved in 200 ml of tetrahydrofuran, and 2 g of Raney nickel are added. The mixture is hydrogenated for 1.5 hours at a hydrogen pressure of 50 bar. The solution is evaporated, dilute hydrochloric acid is added, the mixture is filtered under suction, and the residue is dried.

Yield: 56% of theory
Melting point: 175°–183° C.

The following were prepared analogously to Example 1:

Example 2

Methyl 4-(2-aminophenyl)-2-methyl-5-oxo-1,4,5,7-tetrahydrofuro[3,4-b]pyridine-3-carboxylate

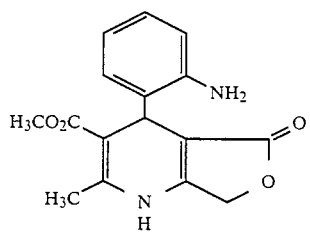

Yield: 80% of theory
Melting point: 193°–195° C.

Example 3

Butyl 4-(2-aminophenyl)-2-methyl-5-oxo-1,4,5,7-tetrahydrofuro[3,4-b]pyridine-3-carboxylate

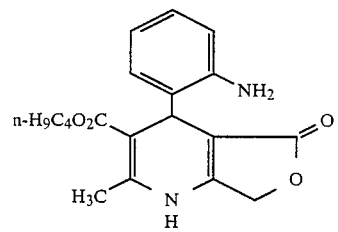

Yield: 60% of theory
Melting point: 167°–169° C.

Example 4

Ethyl 4-(2-benzylaminophenyl)-2-methyl-5-oxo-1,4,5,7-tetrahydrofuro[3,4-b]pyridine-3-carboxylate

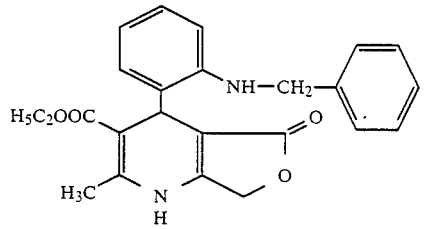

3.5 g (10 mmol) of ethyl 4-(2-aminophenyl)-2-methyl-5-oxo-1,4,5,7-tetrahydrofuro[3,4-b]pyridine-3-carboxylate hydrochloride and 1.4 ml (11 mmol) of benzyl bromide are dissolved in 50 ml of absolute acetone, 1.4 g of potassium carbonate are added, and the mixture is stirred overnight at room temperature. The mixture is concentrated, water is added, and the product is filtered off under suction and recrystallized from methanol.

Yield: 67% of theory
Melting point: 180°–183° C.

The following were prepared analogously to Example 4:

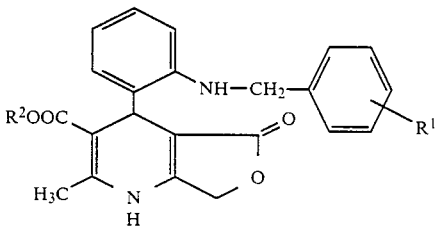

| Example No. | $R^2$ | $R^1$ | Melting point [°C.] | Yield [% of theory] |
|---|---|---|---|---|
| 5 | —$C_2H_5$ | 3-Cl | 165–167 | 55% |
| 6 | —$C_2H_5$ | 3-$H_3C$— | 166–177 | 52% |
| 7 | —$C_2H_5$ | 2-Cl— | 210–217 | 57% |
| 8 | —$C_2H_5$ | 4-$H_3C$— | 166–169 | 50% |
| 9 | —$C_2H_5$ | 4-$NO_2$— | 204–206 | 45% |
| 10 | —$CH_3$ | 4-$H_3C$— | 214 | 40% |
| 11 | —$C_2H_5$ | 4-$C_6H_5$ | 208 | 77% |

-continued

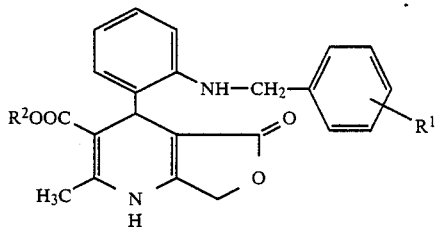

| Example No. | $R^2$ | $R^1$ | Melting point [°C.] | Yield [% of theory] |
|---|---|---|---|---|
| 12 | —CH$_3$ | H | 213 | 40% |

It will be appreciated that the instant specification and claims are set forth by way of illustration and not limitation, and that various modifications and changes may be made without departing from the spirit and scope of the present invention.

What is claimed is:

1. A benzylaminoaryl-dihydropyridinelactone compound of the formula (I)

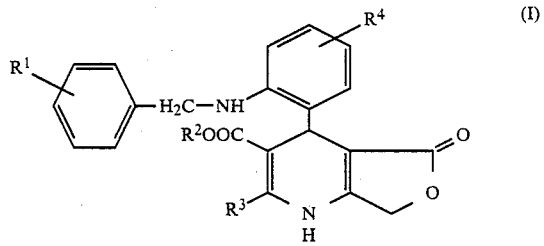

in which
$R^1$ represents hydrogen, halogen, cyano, nitro, $C_6-C_{12}$-aryl, $C_1-C_8$-alkyl, $C_1-C_8$-alkoxy, $C_1-C_6$-alkylthio, trifluoromethyl, trifluoromethoxy, trifluoromethylthio, difluoromethoxy, di-$C_1-C_5$-alkylamino, $C_1-C_6$-alkoxycarbonyl or $C_1-C_6$-alkylsulphonyl,
$R^2$ represents hydrogen, or represents a straight-chain, branched or cyclic, saturated or unsaturated hydrocarbon radical having up to 10 carbon atoms which is optionally substituted by $C_1-C_6$-alkoxy, $C_1-C_6$-alkylthio, $C_1-C_6$-alkylsulphonyl, halogen, cyano, hydroxyl, pyridyl, thienyl, pyrimidyl, piperidinyl, phenyl or an amino group, where the amino group carries two identical or different substituents selected from the group consisting of $C_1-C_5$-alkyl, phenyl and benzyl,
$R^3$ represents $C_1-C_5$-alkyl, or represents cyano, hydroxymethyl or formyl, and
$R^4$ represents hydrogen, halogen, $C_1-C_5$-alkyl or trifluoromethyl,
in the form of its diastereomers, diastereomeric mixtures, racemates or optical antipodes, and physiologically acceptable salts thereof.

2. A compound or salt according to claim 1, wherein
$R^1$ represents hydrogen, fluorine, chlorine, bromine, iodine, cyano, nitro, phenyl, $C_1-C_6$-alkyl, $C_1-C_6$-alkoxy, $C_1-C_4$-alkylthio, trifluoromethyl, trifluoromethoxy, difluoromethoxy, di-$C_1-C_3$-alkylamino, $C_1-C_4$-alkoxycarbonyl or $C_1-C_4$-alkylsulphonyl,
$R^2$ represents hydrogen, or represents a straight-chain or branched hydrocarbon radical which has up to 8 carbon atoms and which is unsubstituted or substituted by $C_1-C_4$-alkoxy, $C_1-C_4$-alkylthio, $C_1-C_4$-alkylsulphonyl, fluorine, chlorine, bromine, iodine, cyano, hydroxyl, pyridyl, pyrimidyl, phenyl or by an amino group, where the amino group carries two identical or different substituents selected from the group consisting of $C_1-C_3$-alkyl and benzyl,
$R^3$ represents $C_1-C_3$-alkyl or cyano, and
$R^4$ represents hydrogen, fluorine, chlorine, bromine, $C_1-C_3$-alkyl or trifluoromethyl.

3. A compound or salt according to claim 1, wherein
$R^1$ represents hydrogen, fluorine, chlorine, bromine, nitro, phenyl, $C_1-C_4$-alkyl, $C_1-C_4$-alkoxy, trifluoromethyl or dimethylamino,
$R^2$ represents straight-chain or branched alkyl which has up to 6 carbon atoms and which is unsubstituted or substituted by methoxy, fluorine, chlorine, cyano, hydroxyl, pyridyl, phenyl or N-benzyl-N-methyl-amino,
$R^3$ represents methyl, and
$R^4$ represents hydrogen, fluorine or chlorine.

4. A compound or salt according to claim 1, wherein said compound has a formula selected from the group consisting of

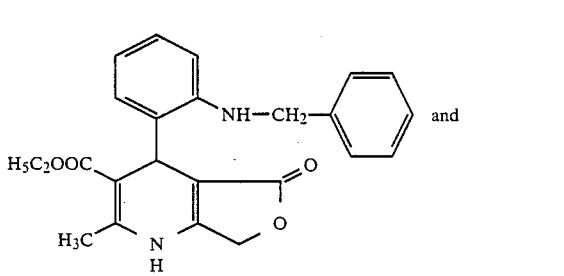 and

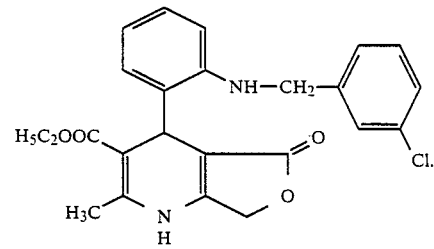

5. A method for the treatment of heart insufficiency and heart-rhythm disorders and/or for improving the contractility of the heart, for improving the tonus of the smooth muscles, for influencing pathologically altered blood pressure, for lowering blood sugar levels, for shrinking mucous membranes and for influencing the salt and liquid balances in a patient in need thereof, which method comprises administering to the patient an amount effective therefor of a compound or a salt according to claim 1.

6. A pharmaceutical composition for the treatment of heart insufficiency and heart rhythm disorders and/or for improving the contractility of the heart comprising an effective amount of a compound according to claim 1 in admixture with a pharmaceutically effective excipient or solvent.

7. A unit dose of a composition according to claim 6 in the form of a tablet, coated tablet, pill, granule, aerosol, syrup, emulsion, suspension or solution.

* * * * *